US00PP33671P2

(12) United States Plant Patent
van SAMBEEK

(10) Patent No.: US PP33,671 P2
(45) Date of Patent: Nov. 23, 2021

(54) ***PHLOX* PLANT NAMED 'DOPHLOSPRIBL'**

(50) Latin Name: *Phlox subulata*
Varietal Denomination: Dophlospribl

(71) Applicant: DUMMEN GROUP B.V., De Lier (NL)

(72) Inventor: Ellen van SAMBEEK, Oegstgeest (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/139,968

(22) Filed: Dec. 31, 2020

(51) Int. Cl.
*A01H 5/02* (2018.01)
*A01H 6/70* (2018.01)

(52) U.S. Cl.
USPC ..... Plt./320
CPC ..... *A01H 6/70* (2018.05)

(58) Field of Classification Search
USPC ..... Plt./320
CPC ..... A01H 6/70; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Phlox* plant named 'Dophlospribl', characterized by its outwardly spreading to creeping and mounding plant habit; vigorous growth habit; freely flowering habit; large light violet-colored flowers with deep violet-colored centers; and good garden performance.

1 Drawing Sheet

Botanical designation: *Phlox subulata.*
Cultivar denomination: 'DOPHLOSPRIBL'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Dümmen Group B.V. of De Lier, The Netherlands on Aug. 12, 2020, application number 2020/1896. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Phlox* plant, botanically known as *Phlox subulata* and hereinafter referred to by the name 'Dophlospribl'.

The new *Phlox* plant is a product of a planned breeding program conducted by the Inventor in Aalsmeer, The Netherlands. The objective of the breeding program was to create new freely-flowering *Phlox* plants with large attractive flowers.

The new *Phlox* plant originated from a cross-pollination made by the Inventor in April, 2010 in Aalsmeer, The Netherlands, of an unnamed proprietary selection of *Phlox subulata*, not patented, as the female, or seed, parent with an unnamed proprietary selection of *Phlox subulata*, not patented, as the male, or pollen, parent. The new *Phlox* plant was discovered and selected by the Inventor as a single flowering plant from within the progeny of the stated cross-pollination in a controlled environment in Aalsmeer, The Netherlands in April, 2011.

Asexual reproduction of the new *Phlox* plant by vegetative cuttings in a controlled environment in Aalsmeer, The Netherlands since June, 2011 has shown that the unique features of this new *Phlox* plant are stable and reproduced true to type in successive generations.

SUMMARY OF THE INVENTION

Plants of the new *Phlox* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dophlospribl'. These characteristics in combination distinguish 'Dophlospribl' as a new and distinct *Phlox* plant:

1. Outwardly spreading to creeping and mounding plant habit.
2. Vigorous growth habit.
3. Freely flowering habit.
4. Large light violet-colored flowers with deep violet-colored centers.
5. Good garden performance.

Plants of the new *Phlox* differ primarily from plants of the parent selections in plant and flowering habit as plants of the new *Phlox* are more uniform and more freely flowering than plants of the parent selections.

Plants of the new *Phlox* can be compared to plants of *Phlox subulata* 'Coral Eyes', not patented. In side-by-side comparisons, plants of the new *Phlox* and 'Coral Eyes' differ in the following characteristics:

1. Plants of the new *Phlox* flower later than plants of 'Coral Eyes'.
2. Plants of the new *Phlox* and 'Coral Eyes' differ in flower color as plants of the new *Phlox* have light violet-colored flowers with deep violet-colored centers whereas plants of 'Coral Eyes' have pink-colored flowers with dark pink-colored centers.

BRIEF DESCRIPTION OF THE PHOTOGRAPH

The accompanying colored photograph illustrates the overall appearance of the new *Phlox* plant showing the colors as true as it is reasonably possible to obtain in colored reproductions of this type. Colors in the photograph may differ slightly from the color values cited in the detailed botanical description which accurately describe the colors of the new *Phlox* plant.

The photograph comprises a side perspective view of typical flowering plant of 'Dophlospribl' grown in a container.

DETAILED BOTANICAL DESCRIPTION

The aforementioned photograph and following observations, measurements and values describe plants grown during the spring in 17-cm containers initially in a glass-covered greenhouse and finished in an outdoor nursery in Aalsmeer, The Netherlands and under cultural practices typical of commercial *Phlox* production. During the production of the plants, day temperatures averaged 21° C. and night temperatures averaged 15° C. Plants were pinched one time two weeks after planting rooted young plants and plants were 45 weeks old when the photograph and the description were taken. In the following description, color references are made to The Royal Horticultural Society Colour Chart, Second Edition, except where general terms of ordinary dictionary significance are used.

Botanical classification: *Phlox subulata* 'Dophlospribl'.

Parentage:

*Female, or seed, parent*.—Unnamed proprietary selection of *Phlox subulata*, not patented.

*Male, or pollen, parent*.—Unnamed proprietary selection of *Phlox subulata*, not patented.

Propagation:

*Type*.—By vegetative cuttings.

*Time to initiate roots, summer*.—About 16 days at temperatures about 26° C.

*Time to initiate roots, winter*.—About three weeks at temperatures about 23° C.

*Time to produce a rooted young plant, summer*.—About 24 days at temperatures about 23° C.

*Time to produce a rooted young plant, winter*.—About four weeks at temperatures about 18° C.

*Root description*.—Medium in thickness, fibrous; typically white to light yellow in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial typically grown as a container and garden plant; outwardly spreading to creeping and mounding plant habit; vigorous growth habit and relatively slow growth rate.

*Plant height*.—About 12 cm.

*Plant width (spread)*.—About 35 cm.

*Lateral branches*.—Branching habit: Freely branching habit with numerous primary and secondary lateral branches developing per plant. Length: About 15 cm. Internode length: About 1 cm. Strength: Strong. Aspect: About 10° from vertical to horizontal. Texture and luster: Smooth, glabrous; glossy. Color: Close to 145B; with development, close to 199D.

Leaf description:

*Arrangement*.—Opposite, decussate; simple; sessile.

*Length*.—About 3.1 cm.

*Width*.—About 3 mm.

*Shape*.—Lanceolate.

*Apex*.—Acuminate.

*Base*.—Cuneate.

*Margin*.—Entire, slightly ciliate.

*Texture and luster, upper and lower surfaces*.—Smooth, glabrous; glossy.

*Venation pattern*.—Hyphodromous.

*Color*.—Developing and fully expanded leaves, upper surface: Close to 141A; venation, close to 141A. Developing and fully expanded leaves, lower surface: Close to 141C; venation, close to 141C.

Flower description:

*Flower type and flowering habit*.—Single rotate and salverform flowers arranged in terminal and lateral panicles; flowers face mostly upright to outwardly depending on position on inflorescence; freely flowering habit with about ten open flowers per inflorescence and about 650 flowers developing per plant during the flowering season.

*Fragrance*.—Slightly fragrant, pleasant.

*Natural flowering season*.—Plants begin flowering about 38 weeks after planting; plants flower in April and May in the garden in The Netherlands; flowers persistent.

*Flower buds*.—Height: About 1.1 cm. Diameter: About 3 mm. Shape: Elliptical. Texture and luster: Smooth, glabrous; matte. Color: Close to 92B.

*Inflorescence height*.—About 9 cm.

*Inflorescence diameter*.—About 7 cm.

*Flower diameter*.—About 2.1 cm to 2.2 cm.

*Flower depth*.—About 1.5 cm.

*Flower throat diameter*.—About 2 mm.

*Flower tube length*.—About 7 mm.

*Flower diameter, proximally*.—About 2 mm.

*Petals*.—Quantity per flower: Typically five in a single whorl; petals fused at the base into a narrow tube. Lobe length: About 1.1 cm. Lobe width: About 8 mm. Lobe shape: Obcordate. Lobe apex: Emarginate. Lobe margin: Entire; slightly undulate. Lobe texture and luster, upper surface: Smooth, glabrous; matte. Lobe texture and luster, lower surface: Smooth, glabrous; semi-glossy. Throat texture and luster: Smooth, glabrous; matte. Tube texture and luster: Smooth, glabrous; semi-glossy. Color: When opening, upper surface: Close to 84B. When opening, lower surface: Close to 91C. Fully opened, upper surface: Close to 91B; towards the throat, close to 95A; venation, close to 91B; color becoming closer to 91D with development. Fully opened, lower surface: Close to 91C; venation, close to 91C; color becoming closer to 91D with development. Throat: Close to 93A; venation, close to 93A. Tube: Close to 92A; venation, close to 92A.

*Sepals*.—Quantity per flower: Typically five in a single whorl, fused towards the base; calyx, tubular in shape. Length: About 7 mm. Width: About 1 mm.

Shape: Narrowly deltoid, subulate. Apex: Acuminate. Margin: Entire. Texture and luster, upper and lower surfaces: Pubescent; glossy. Color: When opening and fully opened, upper surface: Close to 137A tinged with close to 187B. When opening and fully opened, lower surface: Close to 143A.

*Peduncles*.—Length: About 7.5 cm. Diameter: About 2 mm. Strength: Moderately strong. Aspect: About 60° from lateral branch axis. Texture and luster: Pubescent; glossy. Color: Close to 145A.

*Pedicels*.—Length: About 1.8 cm. Diameter: About 1 mm. Strength: Flexible. Aspect: About 5° to 30° from peduncle axis. Texture and luster: Pubescent; glossy. Color: Close to 174A.

*Reproductive organs*.—Stamens: Quantity per flower: Typically five. Filament length: About 1 mm. Filament color: Close to 145C. Anther length: About 1 mm. Anther shape: Elliptical. Anther color: Close to 3A. Pollen amount: Abundant. Pollen color: Close to 17A. Pistils: Quantity per flower: One. Pistil length: About 8 mm. Stigma diameter: About 0.5 mm. Stigma shape: Cleft, three-parted. Stigma color: Close to 145A. Style length: About 5 mm. Style color: Close to 145D. Ovary color: Close to 143B.

*Seeds and fruits*.—To date, seed and fruit development have not been observed on plants of the new *Phlox*.

Garden performance: Plants of the new *Phlox* have been observed to have good garden performance and to tolerate rain, wind, temperatures ranging from −35° C. to 35° C. and to be suitable for USDA Hardiness Zone 3.

Pathogen & pest resistance: To date, plants of the new *Phlox* have not been observed to be resistant to pathogens and pests common to *Phlox* plants.

It is claimed:

1. A new and distinct *Phlox* plant named 'Dophlospribl' as illustrated and described.

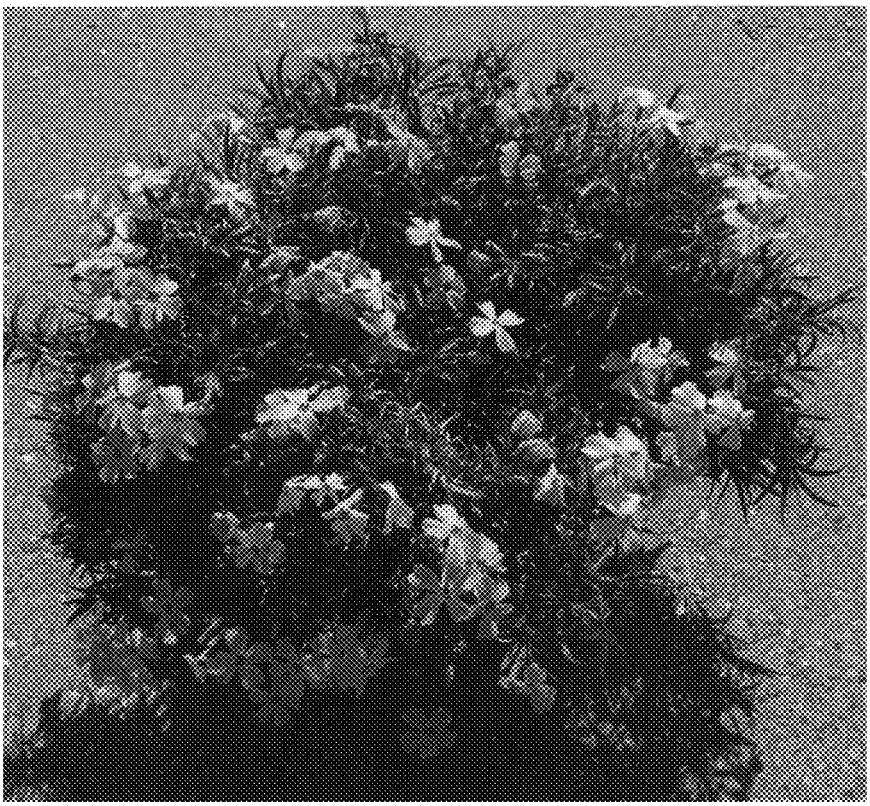

* * * * *